(12) United States Patent
Hwang et al.

(10) Patent No.: US 12,275,653 B2
(45) Date of Patent: Apr. 15, 2025

(54) SYSTEM FOR MONITORING HYDROXYL RADICAL SCAVENGING INDEX IN WATER USING REAL-TIME MULTI-FLUORESCENCE ANALYZER AND PARALLEL FACTOR ANALYSIS APPARATUS, AND METHOD THEREFOR

(71) Applicant: KOREA INSTITUTE OF CIVIL ENGINEERING AND BUILDING TECHNOLOGY, Gyeonggi-do (KR)

(72) Inventors: Tae Mun Hwang, Gyeonggi-do (KR); Sook Hyun Nam, Gyeonggi-do (KR); Eun-Ju Kim, Gyeonggi-do (KR); Jae-Wuk Koo, Gyeonggi-do (KR)

(73) Assignee: KOREA INSTITUTE OF CIVIL ENGINEERING AND BUILDING TECHNOLOGY, Gyeonggi-Do (KR)

( * ) Notice: Subject to any disclaimer, the term of this patent is extended or adjusted under 35 U.S.C. 154(b) by 445 days.

(21) Appl. No.: 17/781,047

(22) PCT Filed: Nov. 19, 2020

(86) PCT No.: PCT/KR2020/016360
§ 371 (c)(1),
(2) Date: May 31, 2022

(87) PCT Pub. No.: WO2021/118099
PCT Pub. Date: Jun. 17, 2021

(65) Prior Publication Data
US 2022/0411287 A1    Dec. 29, 2022

(30) Foreign Application Priority Data
Dec. 9, 2019    (KR) .................. 10-2019-0162387

(51) Int. Cl.
*C02F 1/00* (2023.01)
*C02F 1/32* (2023.01)
(Continued)

(52) U.S. Cl.
CPC ............... *C02F 1/008* (2013.01); *C02F 1/32* (2013.01); *C02F 1/722* (2013.01); *C02F 1/78* (2013.01);
(Continued)

(58) Field of Classification Search
CPC .. C02F 1/008; C02F 1/32; C02F 1/722; C02F 1/78; G01N 21/643; G01N 21/85; G01N 2021/8411
See application file for complete search history.

(56) References Cited

U.S. PATENT DOCUMENTS 9,873,619 B2 * 1/2018 Murayama ........... G01N 21/631
2012/0231549 A1    9/2012 Miller

FOREIGN PATENT DOCUMENTS

JP    2005030839       2/2005
JP    2005030839 A *  2/2005    ............. G01N 21/64
(Continued)

OTHER PUBLICATIONS

KR10-1617822B1_English translation (Year: 2016).*
(Continued)

*Primary Examiner* — Youngsul Jeong
(74) *Attorney, Agent, or Firm* — JCIPRNET

(57) ABSTRACT

Provided are a system for monitoring a hydroxyl radical scavenging index in water using a real-time multi-fluorescence analyzer and a parallel factor analysis apparatus and a method therefor, wherein the system monitors the hydroxyl radical scavenging index in water using the real-time multi-fluorescence analyzer and the parallel factor
(Continued)

analysis apparatus, whereby it is possible to monitor the characteristics of an organic material in target water through a continuous flow analysis method without using an existing indicator material, rhodamine B. In addition, in a water treatment system having an advanced oxidation process (AOP) applied thereto in which ozone, ultraviolet rays, hydrogen peroxide, and the like are combined, it is possible to simply calculate the hydroxyl radical scavenging index in the target water through an organic material characteristic index for each component obtained by classifying the characteristic structure of the organic material in water using real-time fluorescence analysis by means of a parallel factor (PARAFAC) model. Accordingly, the amount of chemical injection and the amount of ultraviolet irradiation, which are process control variables, can be controlled, and under given operating variable conditions, the removal rate of a target material in water is predicted, whereby the system can also be used as a diagnostic tool for process evaluation in the advanced oxidation process. Furthermore, the system can provide operational convenience that enables process control while reducing the amount of power consumed in the advanced oxidation process even though the type of target material and the water quality characteristics of raw water change.

9 Claims, 13 Drawing Sheets

(51) Int. Cl.
*C02F 1/72* (2023.01)
*C02F 1/78* (2023.01)
*G01N 21/64* (2006.01)
*G01N 21/85* (2006.01)
*G01N 21/84* (2006.01)

(52) U.S. Cl.
CPC ........... *G01N 21/643* (2013.01); *G01N 21/85* (2013.01); *G01N 2021/8411* (2013.01)

(56) References Cited

FOREIGN PATENT DOCUMENTS

| | | | | |
|---|---|---|---|---|
| JP | 2014130105 | | 7/2014 | |
| KR | 2014-0064241 A | * | 5/2014 | ................ C02F 1/72 |
| KR | 20140064241 | | 5/2014 | |
| KR | 10-1617822 B1 | * | 5/2016 | ............. G01N 31/22 |
| KR | 101617822 | | 5/2016 | |
| KR | 10-1894834 B1 | * | 9/2018 | ............. C01N 33/18 |
| KR | 101894834 | | 9/2018 | |

OTHER PUBLICATIONS

KR10-1894834B1_English translation (Year: 2018).*
JP-2005030839-A_English translation (Year: 2005).*
KR2014-0064241A_English translation (Year: 2014).*
"International Search Report (Form PCT/ISA/210) of PCT/KR2020/016360," mailed on Mar. 2, 2021, with English translation thereof, pp. 1-5.

* cited by examiner

Natural organic material(NOM)

SYSTEM FOR MONITORING HYDROXYL RADICAL SCAVENGING INDEX IN WATER USING REAL-TIME MULTI-FLUORESCENCE ANALYZER AND PARALLEL FACTOR ANALYSIS APPARATUS, AND METHOD THEREFOR

CROSS-REFERENCE TO RELATED APPLICATION

This application is a 371 application of the International PCT application serial no. PCT/KR2020/016360, filed on Nov. 19, 2020, which claims the priority benefits of Korean Patent Application No. 10-2019-0162387, filed on Dec. 9, 2019. Each of the entirety of the above-mentioned patent applications is hereby incorporated by reference herein and made a part of this specification.

TECHNICAL FIELD

The present invention relates to a system for monitoring a hydroxyl radical scavenging index, and more particularly, to a system for monitoring a hydroxyl radical scavenging index in water using a real-time multi-fluorescence analyzer and a parallel factor analysis apparatus, which are capable of measuring and analyzing the hydroxyl radical scavenging index in real time, in an advanced oxidation process (AOP) of a water treatment system to which ultraviolet rays/hydrogen peroxide, and the like are applied for advanced treatment of trace hazardous materials in potable water or sewage effluent.

BACKGROUND ART

Most water purification plants in Korea use river water as a water source, and since pollution of water sources has recently become more serious due to various pollutants, a water treatment technique for a safe purified water supply is required.

Existing water treatment methods universally use sand filtration and chlorine disinfection methods after coagulation and sedimentation. However, since water treatment methods in the related art have a limitation in efficiently treating drinking water sources containing new pharmaceutical materials (representative substances: carbamazepine, caffeine, and ibuprofen) and trace organic materials such as taste odor causing materials (representative substances: geosmin and 2-methylisoborneol (2-MIB)), various oxidation treatment methods have been studied.

Among such oxidation treatment methods, an advanced oxidation process (AOP) is a technique for removing hard-to-degrade organic materials by maximizing a hydroxyl radical (OH radical; OH·), which is a reaction intermediate product, using ozone, ultraviolet rays, hydrogen peroxide, and the like. This hydroxyl radical (OH radical; OH·) is a material that has the highest oxidizing power, and thus is expected to have an important action in chemical oxidation treatment. Unlike other oxidants, these hydroxide radicals cannot be pre-made and stored and need to be generated directly on-site.

In other words, the hydroxyl radicals produced as intermediates in the process of intermediate decomposition by reacting ozone or UV rays with chemicals such as hydrogen peroxide can play a very important role in water treatment, a method capable of promoting the decomposition of organic materials by increasing the production of hydroxyl radicals according to the decomposition mechanism of ozone/hydrogen peroxide, ozone/ultraviolet rays or ultraviolet rays/hydrogen peroxide has been developed, and the method is referred to as an advanced oxidation process (AOP).

When the AOP is applied to water purification treatment and sewage effluent treatment using the advanced oxidation technique such as ozone/hydrogen peroxide, ozone/ultraviolet rays or ultraviolet rays/hydrogen peroxide, the raw water conditions are different, and when the scavenging of hydroxyl radicals, which may be generated in target treatment water, may be interpreted in order to reduce power consumption, it is possible not only to predict the removal rate of a target material but also to control the appropriate chemical injection conditions and amount of ultraviolet irradiation of the advanced oxidation technique.

Since hydroxyl radicals produced by such an advanced oxidation technique have strong oxidizing power, but have the characteristic of disappearing immediately when they are produced within several milliseconds to several seconds, and greatly affected by a background material such as natural organic material (NOM) and alkalinity, the hydroxyl radicals produced in an advanced oxidation reaction need to be quantified. However, since the ability to produce hydroxyl radicals differs depending on the characteristics of the influent water quality, such as total organic carbon concentration, alkalinity, nitrate nitrogen and the like, a method of accurately monitoring the characteristics by an indirect method is important in terms of process analysis and control.

Meanwhile, as related art, Korean Patent No. 10-1617822, which was filed and registered by the applicant of the present invention, discloses an invention titled "APPARATUS FOR REAL-TIME MEASURING HYDROXYL RADICAL SCAVENGING INDEX IN ADVANCED OXIDATION PROCESS, AND METHOD FOR THE SAME", and will be described with reference to FIG. 1.

FIG. 1 is a configuration view of an apparatus for real-time measuring a hydroxyl radical scavenging index in an advanced oxidation process according to the technique in the related art.

Referring to FIG. 1, an apparatus 10 for real-time measuring a hydroxyl radical scavenging index according to the technique in the related art roughly includes a sample unit 11, a reagent unit 12, an ultraviolet reaction unit 13, an indicator material detection unit 14 and a data analysis unit 15.

The sample unit 11 supplies target raw water to a continuous flow injection pipeline 16.

The reagent unit 12 supplies a reagent consisting of rhodamine B 12a which is an indicator material, hydrogen peroxide 12b and distilled water 12c to the continuous flow injection pipeline 16. In this case, rhodamine B is used as an indicator material, and in this case, since rhodamine B is a staining material, rhodamine B may be adsorbed into a tube in which a sample 11 moves. Therefore, it is desirable to use a material that is less stained, is easily accumulated, and is less easily removed by a tube.

The ultraviolet reaction unit 13 includes a quartz cell 13a and an ultraviolet lamp 13b, and is connected to the continuous flow injection pipeline 16 to which the sample unit 11 and the reagent unit 12 are connected by a continuous flow injection method.

The indicator material detection unit 14 uses a spectrophotometer, and measures the concentration of rhodamine B, which is an indicator material after a reaction in the ultraviolet reaction unit 13.

The data analysis unit 15 has a built-in numerical calculation algorithm for data acquisition and signal processing.

In the case of an apparatus for real-time measuring a hydroxyl radical scavenging index of the advanced oxidation process according to the technique in the related art, the concentration of hydrogen peroxide whose dilution ratio is adjusted with distilled water and an indicator material rhodamine B can be measured in real time by applying a continuous flow injection method that changes the flow rate of a sample and constantly keeps the intensity of ultraviolet rays on a single continuous flow injection pipeline in an advanced oxidation process of ultraviolet rays/hydrogen peroxide, which is applied to the treatment of harmful materials using hydroxyl radicals as a major mechanism.

Further, in the case of an apparatus for real-time measuring a hydroxyl radical scavenging index of an advanced oxidation process according to the technique in the related art, it is possible to accurately calculate the ability to quantitatively remove harmful materials removed by an advanced oxidation process of ultraviolet rays/hydrogen peroxide, an amount of ultraviolet irradiation and an amount of hydrogen peroxide introduced by real-time measuring a hydroxyl radical scavenging index in the advanced oxidation process applied in order to remove trace organic pollutants in advanced potable water treatment or sewage effluent.

In the case of an apparatus for real-time measuring a hydroxyl radical scavenging index of an advanced oxidation process according to the technique in the related art, a hydroxyl radical scavenging index can be measured by applying a continuous flow injection analysis (FIA) principle using an indicator material rhodamine B to react ultraviolet rays/hydrogen peroxide in a reaction tube.

Although an apparatus for real-time measuring a hydroxyl radical scavenging index of the advanced oxidation process according to the technique in the related art is a new method using an indicator material rhodamine B by a continuous flow injection analysis method in a water treatment technique restricted to a process of ultraviolet rays/hydrogen peroxide, the hydroxyl radical scavenging index is measured once per hour by measuring the index at a flow rate ratio for each measurement step when the structure of a reactor is a single reactor, so there is a problem in that a lot of time is taken.

As another related art for solving the problems of the apparatus for real-time measuring a hydroxyl radical scavenging index of the advanced oxidation process according to the above-described technique in the related art. Korean Patent No. 10-1894834, which was filed and registered by the applicant of the present invention, discloses an invention titled "METHOD FOR OPTIMIZING PROCESS CONTROL VARIABLE OF ADVANCED OXIDATION PROCESS USING RADICAL INDEX DETERMINING APPARATUS WITH MULTI-CHANNEL CONTINUOUS FLOW REACTOR", and will be described with reference to FIG. 2.

FIG. 2 is a configuration view of an apparatus for measuring a radical index, which is equipped with a multi-channel continuous flow reactor according to the technique in the related art.

Referring to FIG. 2, an apparatus 20 for measuring a radical index, which is equipped with a multi-channel continuous flow reactor according to the technique in the related art, is an apparatus for measuring a radical index by an automated sequential injection analysis method in a water treatment technique to which an advanced oxidation process using ultraviolet rays is applied, and includes a sample supply unit 21, a reagent supply unit 22, an ultraviolet reaction unit 23, an indicator material detection unit 24, and a data analysis and process control unit 25.

The sample supply unit 21 supplies raw water to be treated to a continuous flow injection pipeline 26 through a sample supply pump 27a.

The reagent supply unit 22 supplies a reagent including an indicator material rhodamine B 22a, hydrogen peroxide 22b and distilled water 22c to the continuous flow injection pipeline 26 through each reagent supply pump 27b, 27c and 27d. In this case, rhodamine B is used as the indicator material, and in this case, since the rhodamine B is a staining material, rhodamine B may be adsorbed into a tube in which a sample 210 moves.

The ultraviolet reaction unit 23 includes a multi-channel continuous flow reactor 23a, an automatic distributor 23b, a reactor cell 23c and an ultraviolet lamp 23d, and is connected to the continuous flow injection pipeline 26 to which the sample supply unit 21 and the reagent supply unit 22 are connected by a continuous flow injection method.

The indicator material detection unit 24 uses a spectrophotometer implemented with an optical cable, and measures the concentration of rhodamine B, which is the indicator material, after a reaction in the ultraviolet reaction unit 23.

The data analysis and process control unit 25 may be implemented, for example, by a computer, collects and analyzes data from the indicator material detection unit 24, and calculates optimized values of the amount of ultraviolet irradiation and the injection amount of hydrogen peroxide, which are control variables for removing a target pollutant while minimizing process energy used in the advanced oxidation process using the measured radical index.

Specifically, an apparatus 20 for measuring a radical index, which is equipped with a multi-channel continuous flow reactor according to the technique in the related art measures the reduction rate of rhodamine B 22a by injecting a constant concentration of an indicator material rhodamine B 22a and manually analyzing the intensity of ultraviolet irradiation and the concentration conditions of hydrogen peroxide at each step several times in order to measure the radical index of a sample which is target raw water.

Accordingly, in the case of a process control variable optimization method of an advanced oxidation process using an apparatus for measuring a radical index, which is equipped with a multi-channel continuous flow reactor according to the technique in the related art, it is possible to measure a radical index by an apparatus for measuring a radical index for a sequential injection analysis, which is equipped with a multi-channel continuous flow reaction tube rather than a single flow tube and calculate a combination of the amount of ultraviolet irradiation and the injection amount of hydrogen peroxide that minimizes the radical process energy therefrom.

In the case of a process control variable optimization method of an advanced oxidation process using an apparatus for measuring a radical index, which is equipped with a multi-channel continuous flow reactor according to the technique in the related art, in a water treatment system to which an advanced oxidation process (AOP) using ultraviolet rays is applied, process diagnosis that predicts the ability to remove harmful materials in water may be performed using a sequential injection analysis apparatus for measuring a radical index, which is equipped with a multi-channel continuous flow reactor and a process simulation program including a process energy optimized interpretation model. In addition, energy can be saved and operational convenience can be provided by calculating the amount of ultraviolet irradiation and the injection amount of hydrogen peroxide which minimize the energy to perform process control of the advanced oxidation process.

In the case of a process control variable optimization method of an advanced oxidation process using an apparatus for measuring a radical index, which is equipped with a multi-channel continuous flow reactor according to the technique in the related art, process performance may be maximized while minimizing the process energy of an advanced oxidation process using ultraviolet rays by maximizing a hydroxyl radical (OH) so as to remove harmful organic pollutants, and real-time process diagnosis and process control are also enabled by an apparatus for measuring a radical index, which is equipped with a multi-channel continuous flow reactor.

However, in the case of a process control variable optimization method of an advanced oxidation process using an apparatus for measuring a radical index, which is equipped with a multi-channel continuous flow reactor according to the technique in the related art, when an indicator material rhodamine B is used for a long period of time, there is a problem in that a color-developing reagent is adsorbed into a reaction tube, and thus the tube needs to be periodically washed.

DISCLOSURE

Technical Problem

A technical object to be achieved by the present invention for solving the above-described problems is to provide a system for monitoring a hydroxyl radical scavenging index in water using a real-time multi-fluorescence analyzer and a parallel factor analysis apparatus and a method therefor, wherein the system monitors the hydroxyl radical scavenging index in water using the parallel factor analysis apparatus, whereby it is possible to monitor the characteristics of an organic material in target water through a continuous flow analysis method without using an existing indicator material, rhodamine B.

Another technical object to be achieved by the present invention is to provide a system for monitoring a hydroxyl radical scavenging index in water using a real-time multi-fluorescence analyzer and a parallel factor analysis apparatus and a method therefor, wherein in a water treatment system having an advanced oxidation process (AOP) applied thereto to which ozone, ultraviolet rays, hydrogen peroxide, and the like are combined, it is possible to simply calculate the hydroxyl radical scavenging index in the target water through an organic material characteristic index for each component obtained by classifying the characteristic structure of the organic material in water using real-time fluorescence analysis by means of a parallel factor (PARAFAC) model.

Still another technical object to be achieved by the present invention is to provide a system for monitoring a hydroxyl radical scavenging index in water using a real-time multi-fluorescence analyzer and a parallel factor analysis apparatus and a method therefor, wherein the system can provide operational convenience that enables process control while reducing the amount of power consumed in the advanced oxidation process even though the type of target material and the water quality characteristics of raw water change.

Technical Solution

As a means for achieving the above-described technical objects, the system for monitoring a hydroxyl radical scavenging index in water using a real-time multi-fluorescence analyzer and a parallel factor analysis apparatus according to the present invention includes: a target water supply unit that supplies target water which is water to be treated by an advanced oxidation process (AOP); a real-time multi-fluorescence analyzer that consists of multiple channels and generates excitation-emission matrix (EEM) data by measuring the fluorescence of a natural organic material in the target water; a parallel factor analysis apparatus that classifies the EEM data by component for the multi-fluorescence analysis of the EEM data; an organic material characteristic index derivation unit that derives an organic material characteristic index for each component; a hydroxyl radical scavenging index calculation unit that calculates a hydroxyl radical scavenging index in the target water corresponding to the organic material characteristic index for each component; and a process control variable monitoring unit that monitors process control variables using a reaction rate model, wherein the characteristics of the organic material in the target water are monitored through a continuous flow analysis method.

Here, the target water may be raw water to be treated by an advanced oxidation process or treated water to be treated by an advanced oxidation process.

Here, the real-time multi-fluorescence analyzer may generate excitation-emission matrix (EEM) data using a plurality of fluorescence analysis apparatuses that emit three wavelength bands so as to measure the fluorescence of a natural organic material (NOM) in the target water.

Here, the parallel factor analysis apparatus classifies the EEM data by first, second and third components by parallel factor (PARAFAC) modeling, wherein the first component classifies the EEM data using an excitation wavelength of 250 to 260 nm and an emission wavelength of 380 to 480 nm, the second component classifies the EEM data using an excitation wavelength of 330 to 350 nm and an emission wavelength of 420 to 480 nm, and the third component classifies the EEM data using an excitation wavelength of 270 to 280 nm and an emission wavelength of 320 to 350 nm.

Here, the parallel factor modeling applies a 3D-PRAFAC model that three-dimensionally analyzes the EEM data by dividing the EEM data into each of three factors of a, b and c, wherein the EEM data array ($x_{ijk}$) of the 3D-PARAFAC model is given as $$x_{ijk} = \sum_{f=1}^{F} a_{if} b_{jf} c_{kf} + e_{ijk},$$

is represented by three matrices A, B and C having elements $a_{if}$, $b_{jj}$ and $c_{kj}$ in this case, and is established when the sum of error components ($e_{ijk}$) becomes a minimum.

Here, the process control variable monitoring unit may calculate and control the amount of chemical injection or the amount of ultraviolet irradiation which is applied to the advanced oxidation process.

The system for monitoring a hydroxyl radical scavenging index in water using a real-time multi-fluorescence analyzer and a parallel factor analysis apparatus according to the present invention may additionally include a target material removal rate prediction unit that predicts the removal rate of the target material in water for the process evaluation diagnosis of the advanced oxidation process.

Meanwhile, as a means for achieving the above-described technical objects, the method for monitoring a hydroxyl radical scavenging index in water using a real-time multi-fluorescence analyzer and a parallel factor analysis apparatus according to the present invention includes: a) supplying target water which is water to be treated by an advanced oxidation process; b) generating EEM data by measuring the fluorescence of a natural organic material in target water through a real-time multi-fluorescence analyzer consisting of multiple channels; c) analyzing the multi-fluorescence of the EEM data and classifying the EEM data by component through a parallel factor analysis apparatus; d) deriving an organic material characteristic index for each component; e) calculating a hydroxyl radical scavenging index in the target water corresponding to the organic material characteristic index for each component; and f) monitoring process control variables using a reaction rate model, wherein the characteristics of the organic material in the target water are monitored through a continuous flow analysis method.

Advantageous Effects

According to the present invention, the characteristics of an organic material in target water can be monitored through a continuous flow analysis method without using an existing indicator material rhodamine B by monitoring a hydroxyl radical scavenging index in water using a real-time fluorescence analyzer and a parallel factor analysis apparatus. Accordingly, since it is possible to avoid the trouble of periodically washing the indicator material adsorbed into a reaction tube, a real-time multi-fluorescence analysis and measurement apparatus for automated monitoring of the hydroxyl radical requirement index in water can be provided.

According to the present invention, in a water treatment system having an advanced oxidation process (AOP) applied thereto in which ozone, ultraviolet rays, hydrogen peroxide, and the like are combined, it is possible to simply calculate the hydroxyl radical scavenging index in the target water through an organic material characteristic index (fluorescence index) for each component obtained by classifying the characteristic structure of the organic material in water using real-time fluorescence analysis by means of a parallel factor (PARAFAC) model. Accordingly, the amount of chemical injection and the amount of ultraviolet irradiation, which are process control variables, can be controlled, and under given operating variable conditions, the removal rate of a target material in water is predicted, whereby the system can also be used as a diagnostic tool for process evaluation in the advanced oxidation process.

According to the present invention, the system can provide operational convenience that enables process control while reducing the amount of power consumed in the advanced oxidation process even though the type of target material and the water quality characteristics of raw water change.

MODES OF THE INVENTION

Figure 1:
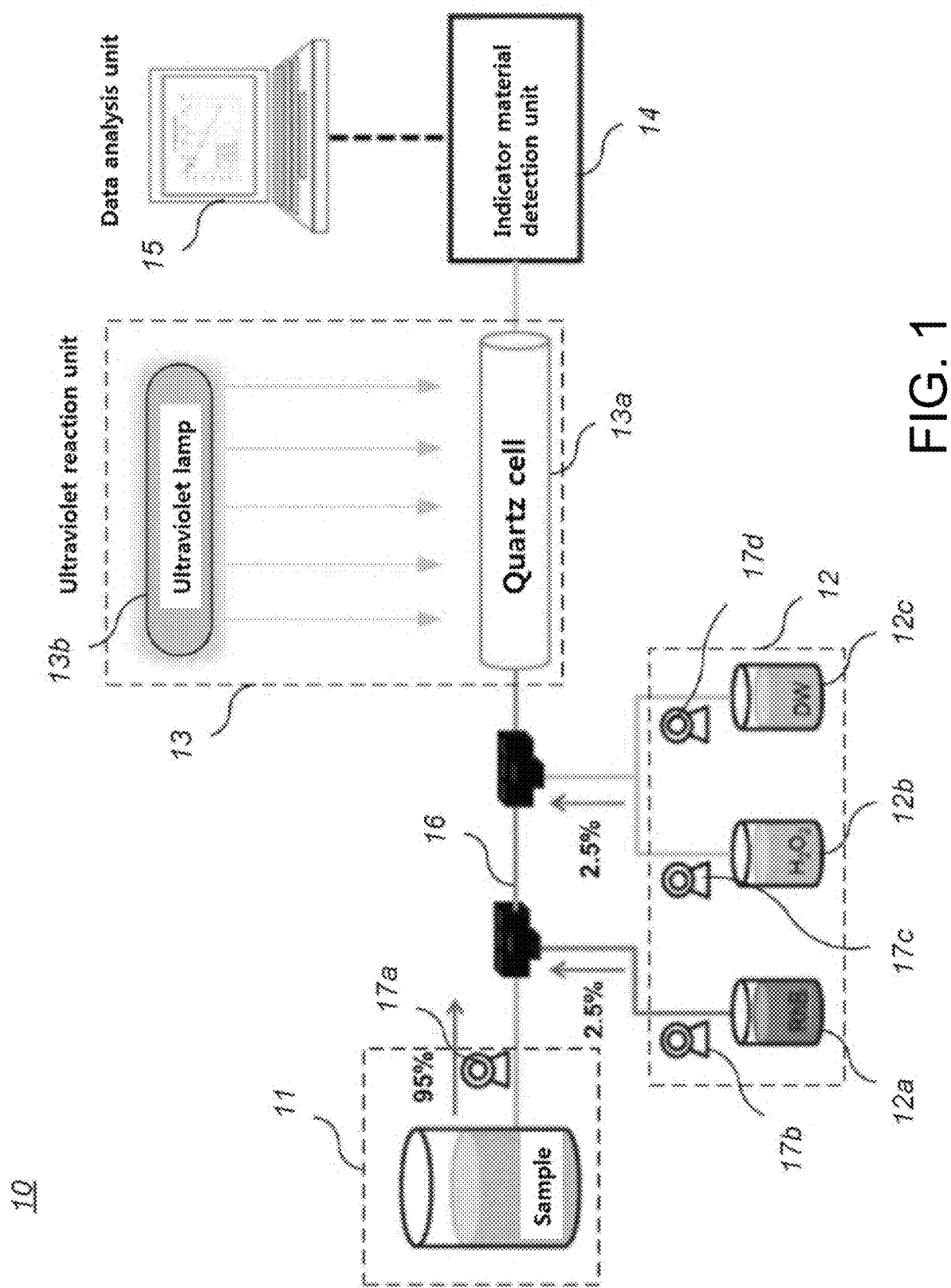
FIG. 1 is a configuration view of an apparatus for real-time measuring a hydroxyl radical scavenging index in an advanced oxidation process according to the technique in the related art.
Figure 2:
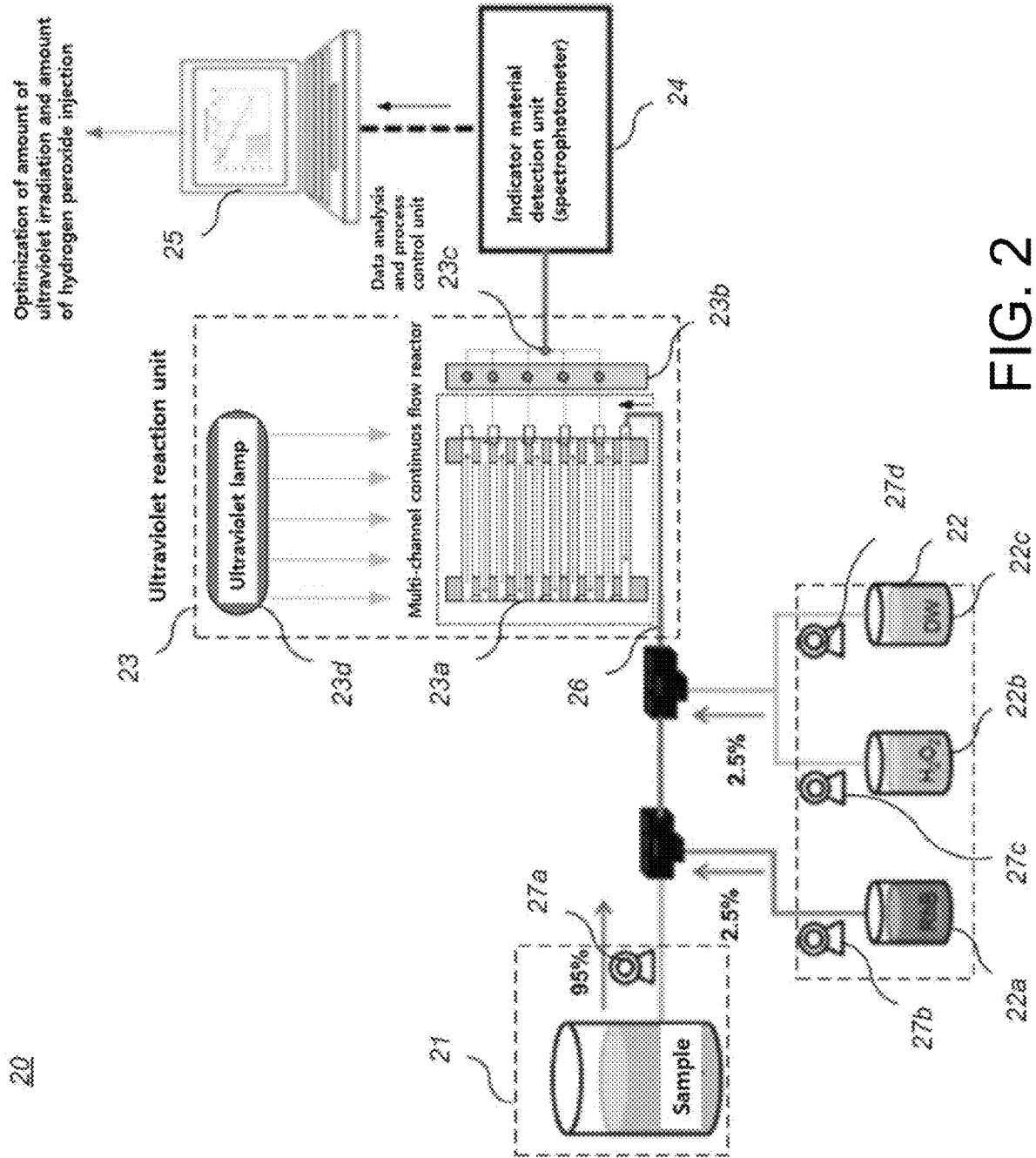
FIG. 2 is a configuration view of an apparatus for measuring a radical index, which is equipped with a multi-channel continuous flow reactor according to the technique in the related art.

Included are a target water supply unit 110 that supplies target water which is water to be treated by an advanced oxidation process (AOP); a real-time multi-fluorescence analyzer 120 that consists of multiple channels and generates excitation-emission matrix (EEM) data by measuring the fluorescence of a natural organic material (NOM) in the target water; a parallel factor analysis apparatus 130 that classifies the EEM data by component for the multi-fluorescence analysis of the EEM data; an organic material characteristic index derivation unit 140 that derives an organic material characteristic index (fluorescence index) for each component; a hydroxyl radical scavenging index calculation unit 150 that calculates a hydroxyl radical scavenging index in the target water corresponding to the organic material characteristic index for each component; and a process control variable monitoring unit 160 that monitors process control variables using a reaction rate model, wherein the characteristics of the organic material in the target water are monitored through a continuous flow analysis method.

Hereinafter, exemplary embodiments of the present invention will be described in detail with reference to the accompanying drawings such that a person with ordinary skill in the art to which the present invention pertains can easily carry out the present invention. However, the present invention may be implemented in various different forms, and is not limited to the exemplary embodiments described herein. In addition, in order to clearly describe the present invention, portions that are not related to the description are omitted in the drawings, and like reference numerals are added to like portions throughout the specification.

Throughout the present specification, when one part "includes" one constituent element, unless otherwise specifically described, this does not mean that another constituent element is excluded, but means that another constituent element may be further included. Further, a term such as " . . . part" described in the specification means a unit for processing at least one function or operation, and this may be realized by hardware or software, or by combining hardware or software.

[System 100 for Monitoring Hydroxyl Radical Scavenging Index in Water Using Real-Time Multi-Fluorescence Analyzer and Parallel Factor Analysis Apparatus]

Figure 3:
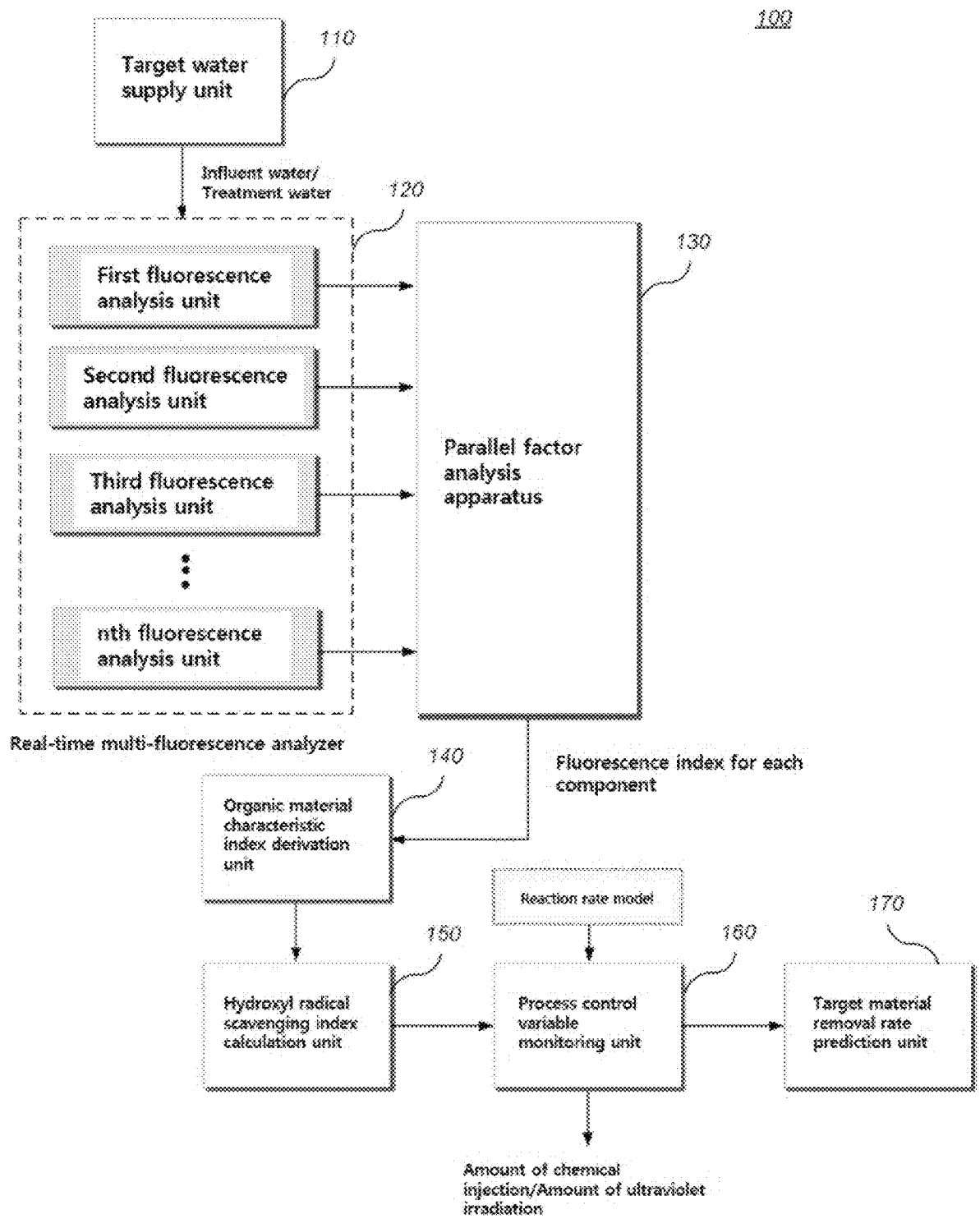
FIG. 3 is a configuration view of a system for monitoring a hydroxyl radical scavenging index in water using a real-time multi-fluorescence analyzer and a parallel factor analysis apparatus according to exemplary embodiments of the present invention.

FIG. 3 is a configuration view of a system for monitoring a hydroxyl radical scavenging index in water using a real-time multi-fluorescence analyzer and a parallel factor analysis apparatus according to exemplary embodiments of the present invention.

Referring to FIG. 3, a system 100 for monitoring a hydroxyl radical scavenging index in water using a real-time multi-fluorescence analyzer and a parallel factor analysis apparatus according to exemplary embodiments of the present invention includes a target water supply unit 110, a real-time multi-fluorescence analyzer 120, a parallel factor analysis apparatus 130, an organic material characteristic index derivation unit 140, a hydroxyl radical scavenging index calculation unit 150, a process control variable monitoring unit 160 and a target material removal rate prediction unit 170.

The target water supply unit 110 supplies target water which is water to be treated by an advanced oxidation process (AOP). Here, the target water may be raw water to be treated by an advanced oxidation process (AOP) or a treated water to be treated by an advanced oxidation process (AOP).

The real-time multi-fluorescence analyzer 120 consists of multiple channels of first to nth fluorescence analyzers capable of continuously monitoring a hydroxyl radical scavenging index in water, and generates excitation-emission matrix (EEM) data by measuring the fluorescence of a natural organic material (NOM) in the target water. For example, the real-time multi-fluorescence analyzer 120 may generate the EEM data using a plurality of fluorescence analyzers that emit three wavelength bands so as to measure the fluorescence of a natural organic material (NOM) in the target water. In this case, the real-time multi-fluorescence analyzer 120 may perform multiplex fluorescence analysis in the wavelength bands for each of the influent raw water and the treated water.

The parallel factor analysis apparatus 130 classifies the EEM data by component for the multi-fluorescence analysis of the EEM data. In this case, the parallel factor analysis apparatus 130 classifies the EEM data by first, second and third components by parallel factor (PARAFAC) modeling, wherein the first component classifies the EEM data using an excitation wavelength of 250 to 260 nm and an emission wavelength of 380 to 480 nm, the second component classifies the EEM data using an excitation wavelength of 330 to 350 nm and an emission wavelength of 420 to 480 nm, and the third component classifies the EEM data using an excitation wavelength of 270 to 280 nm and an emission wavelength of 320 to 350 nm.

The organic material characteristic index derivation unit 140 derives an organic material characteristic index (fluorescence index) for each component.

The hydroxyl radical scavenging index calculation unit 150 calculates a hydroxyl radical scavenging index in the target water corresponding to the organic material characteristic index for each component.

The process control variable monitoring unit 160 monitors process control variables using a reaction rate model. In this case, the process control variable monitoring unit may calculate and control the amount of chemical injection or the amount of ultraviolet irradiation which is applied to the advanced oxidation process (AOP).

The target material removal rate prediction unit 170 predicts the removal rate of a target material in water for process evaluation diagnosis.

Figure 4:
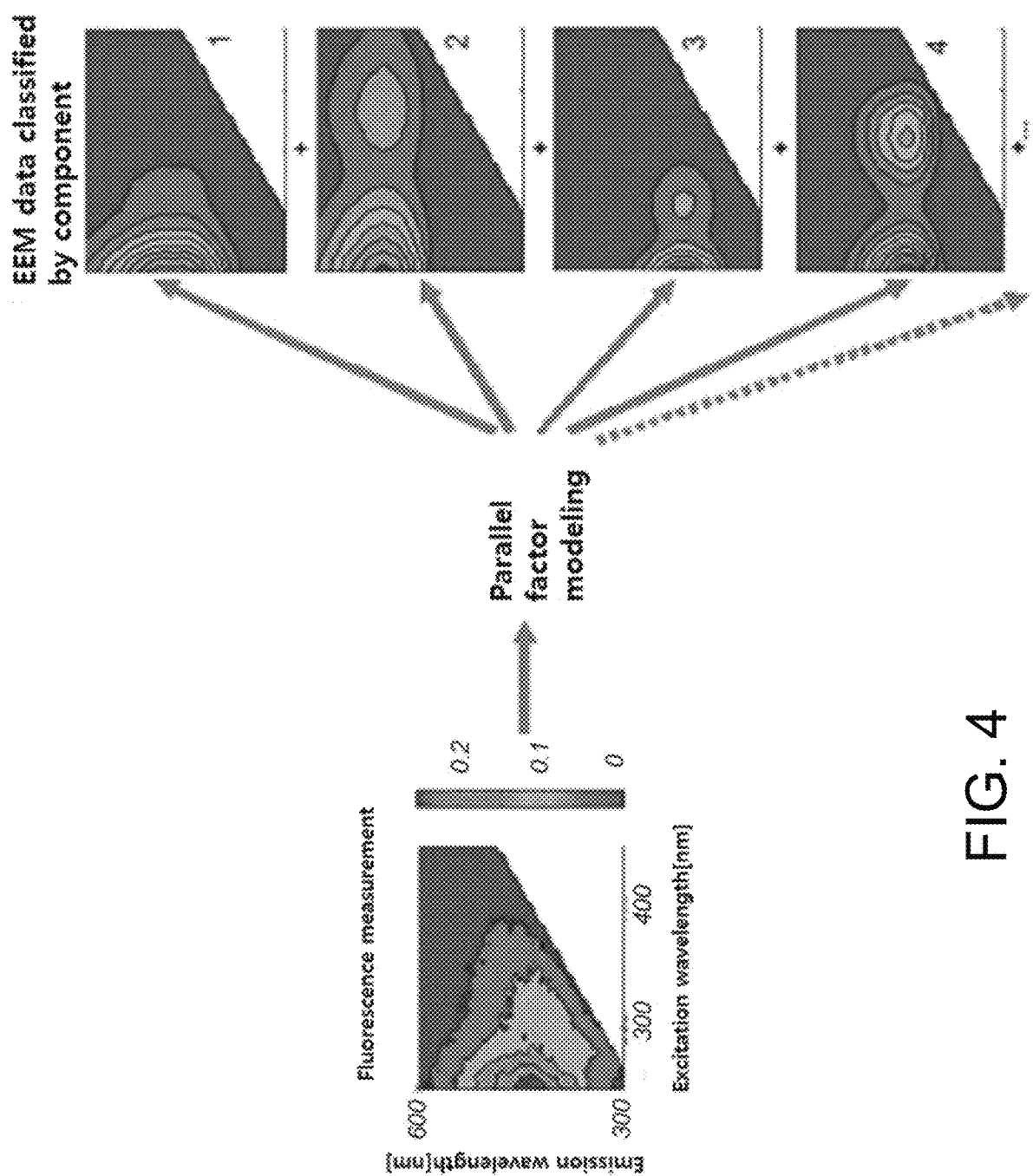
FIG. 4 is a view for describing the parallel factor analysis principle in a system for monitoring a hydroxyl radical scavenging index in water using a real-time multi-fluorescence analyzer and a parallel factor analysis apparatus according to exemplary embodiments of the present invention.

Meanwhile, FIG. 4 is a view for describing the parallel factor analysis principle in a system for monitoring a hydroxyl radical scavenging index in water using a real-time multi-fluorescence analyzer and a parallel factor analysis apparatus according to exemplary embodiments of the present invention.

In general, since a dissolved organic material is a heterogeneous complex consisting of complex chemical structures, in order to grasp information on these types of complexes more accurately, a superimposed fluorescence intensity that appears on 3D-EEM needs to be considered by dividing the intensity into specific emission wavelength regions.

Accordingly, in the case of a system for monitoring a hydroxyl radical scavenging index in water using a real-time multi-fluorescence analyzer and a parallel factor analysis apparatus according to exemplary embodiments of the present invention, as illustrated in FIG. 4, parallel factor modeling is performed using the parallel factor analysis apparatus 130.

Figure 5:
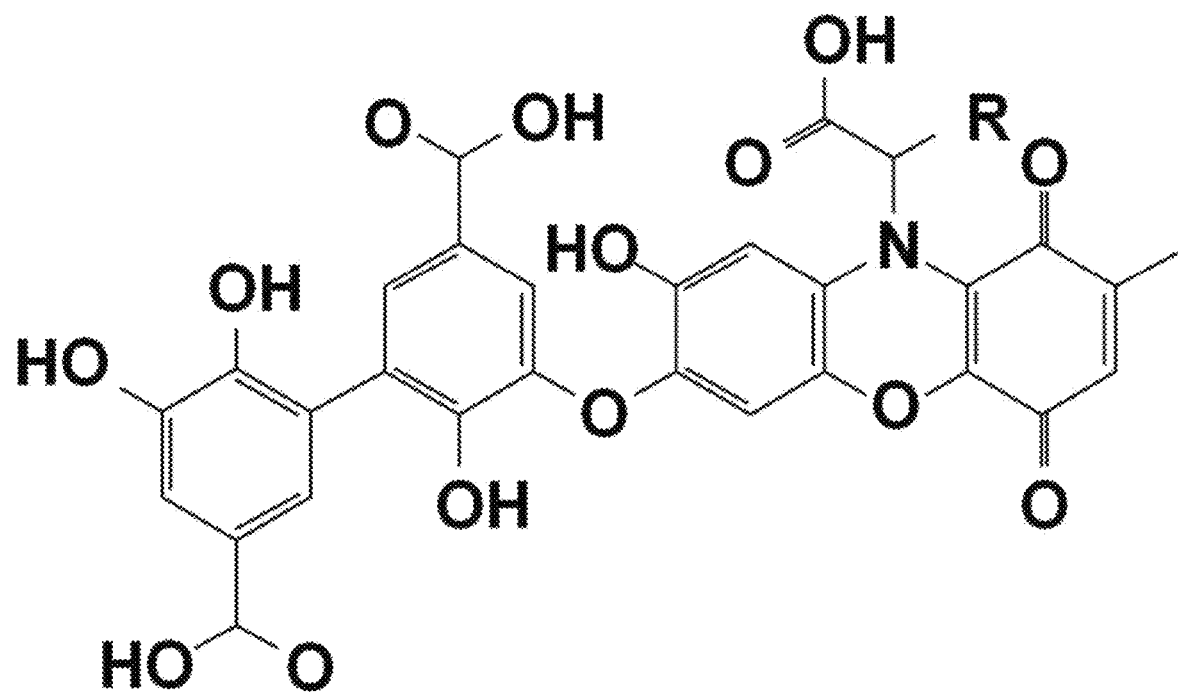
FIG. 5 is a view which exemplifies a natural organic material (NOM) included in target water in a system for monitoring a hydroxyl radical scavenging index in water using a real-time multi-fluorescence analyzer and a parallel factor analysis apparatus according to exemplary embodiments of the present invention.
Figure 6:
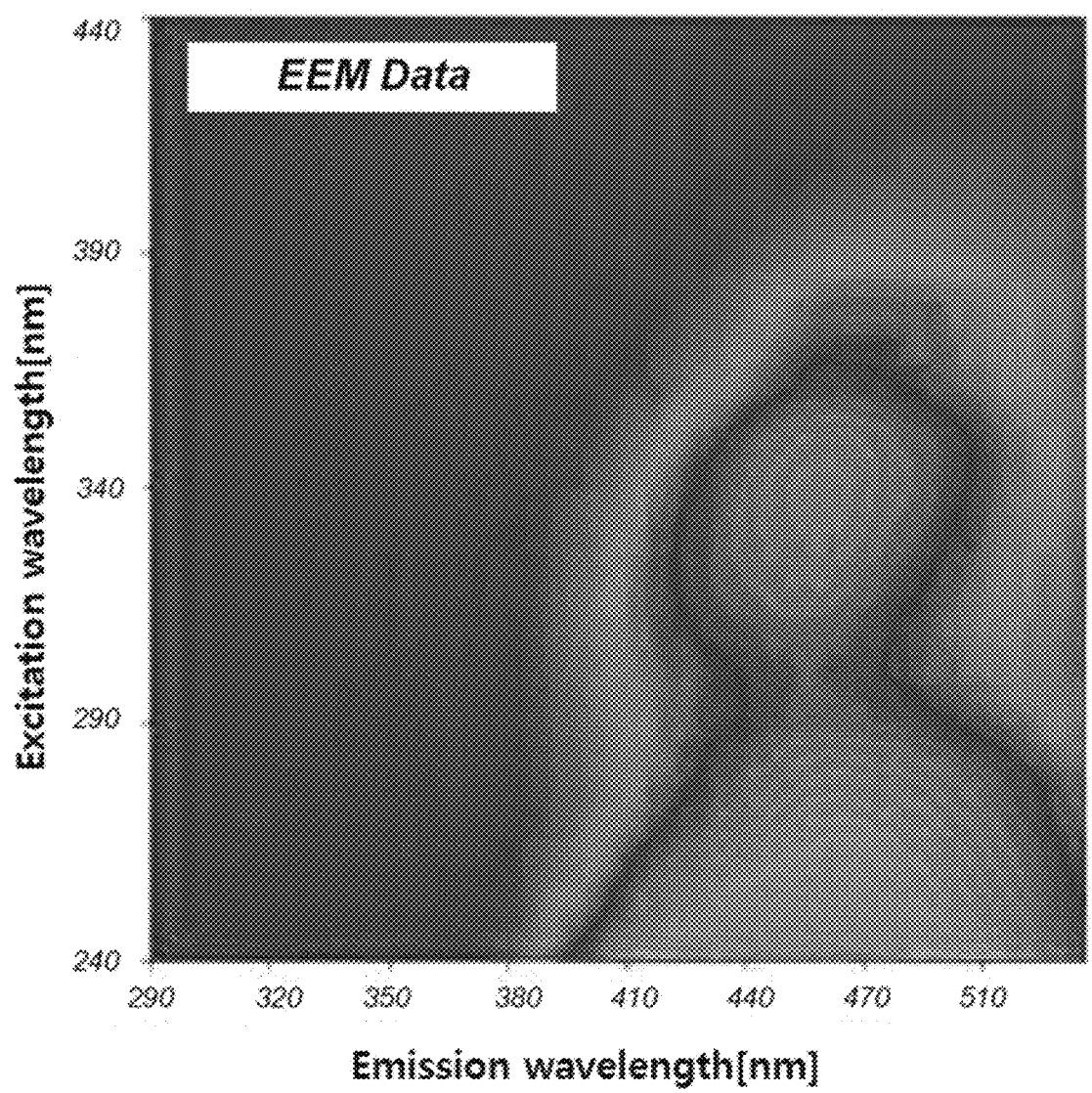
FIG. 6 is a view illustrating EEM data measured by the real-time multi-fluorescence analyzer in a system for monitoring a hydroxyl radical scavenging index in water using a real-time multi-fluorescence analyzer and a parallel factor analysis apparatus according to exemplary embodiments of the present invention.

Meanwhile, FIG. 5 is a view which exemplifies a natural organic material (NOM) included in target water in a system for monitoring a hydroxyl radical scavenging index in water using a real-time multi-fluorescence analyzer and a parallel factor analysis apparatus according to exemplary embodiments of the present invention, and FIG. 6 is a view illustrating EEM data measured by the real-time multi-fluorescence analyzer in a system for monitoring a hydroxyl radical scavenging index in water using a real-time multi-fluorescence analyzer and a parallel factor analysis apparatus according to exemplary embodiments of the present invention.

The natural organic material (NOM) as illustrated in FIG. 5 is a natural product formed by putrefaction of animals, plants, and the like, is produced through other pathways such as putrefaction or microbial decomposition, and shows very different characteristics by region, season, water system, and country. For example, this is because natural organic materials in a specific area have very high hydrophobicity (typical example, humic acid), whereas natural organic materials in other areas may have high hydrophilicity and high microbial degradability Nutrients (particularly nitrogen and phosphorus) contained in such natural organic materials as limiting factors that control the growth of microorganisms also affect an eutrophication phenomenon that occurs in a water system such as lakes and marshes in the summer. Natural organic materials present in the water system plays an important role in the organic material circulation, climate change, and the like in the aquatic ecosystem.

Accordingly, in the case of a system for monitoring a hydroxyl radical scavenging index in water using a real-time multi-fluorescence analyzer and a parallel factor analysis apparatus according to exemplary embodiments of the present invention, as illustrated in FIG. 6, the real-time multi-fluorescence analyzer 120 generates excitation-emission matrix (EEM) data by measuring the fluorescence of a natural organic material (NOM) in the target water.

In this case, the real-time multi-fluorescence analyzer 120 may generate the EEM data using a plurality of fluorescence analyzers that emit three wavelength bands so as to measure the fluorescence of a natural organic material (NOM) in the target water.

Figure 7:
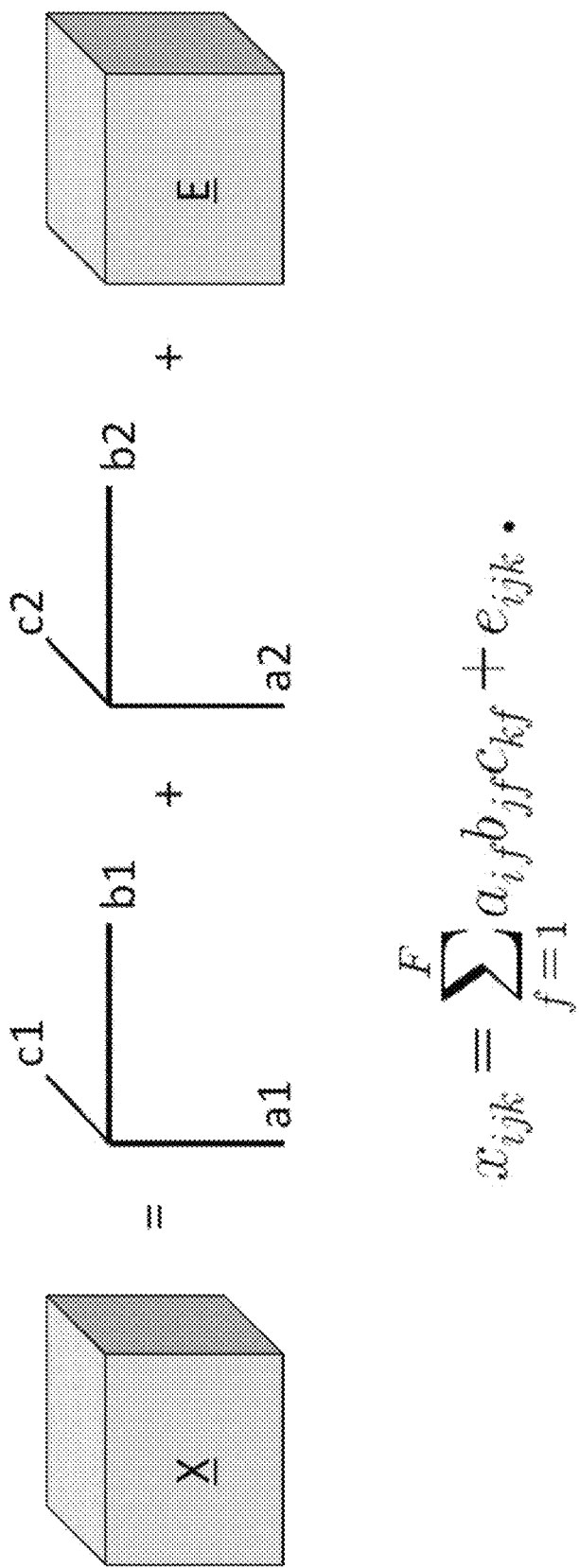
FIG. 7 is a view for describing 3D-parallel factor (PARAFAC) modeling applied to a system for monitoring a hydroxyl radical scavenging index in water using a real-time multi-fluorescence analyzer and a parallel factor analysis apparatus according to exemplary embodiments of the present invention.
Figure 8:
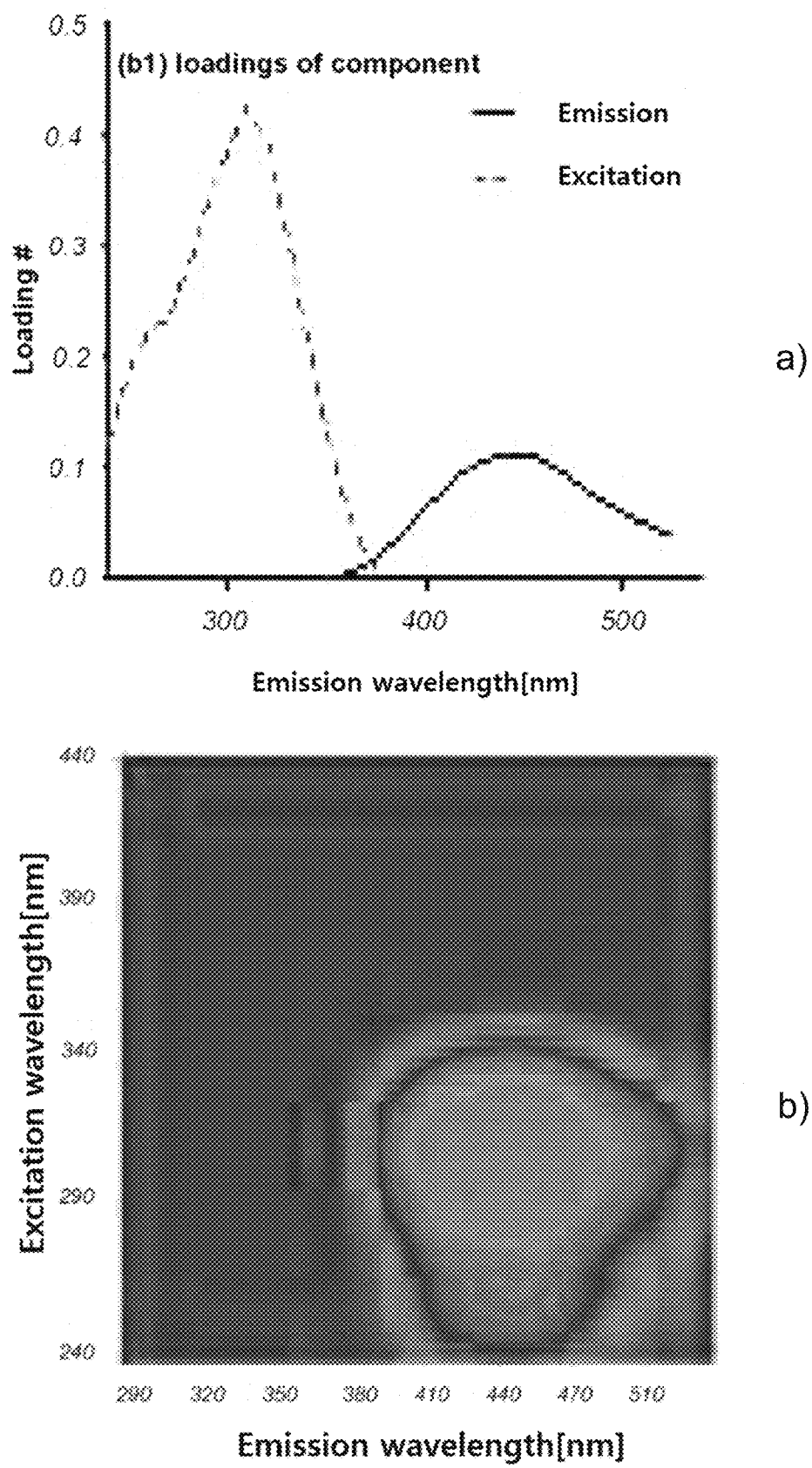
FIGS. 8 to 12 are views each illustrating the parallel factor (PARAFAC) modeling results of the parallel factor analysis apparatus in a system for monitoring a hydroxyl radical scavenging index in water using a real-time multi-fluorescence analyzer and a parallel factor analysis apparatus according to exemplary embodiments of the present invention.
Figure 9:
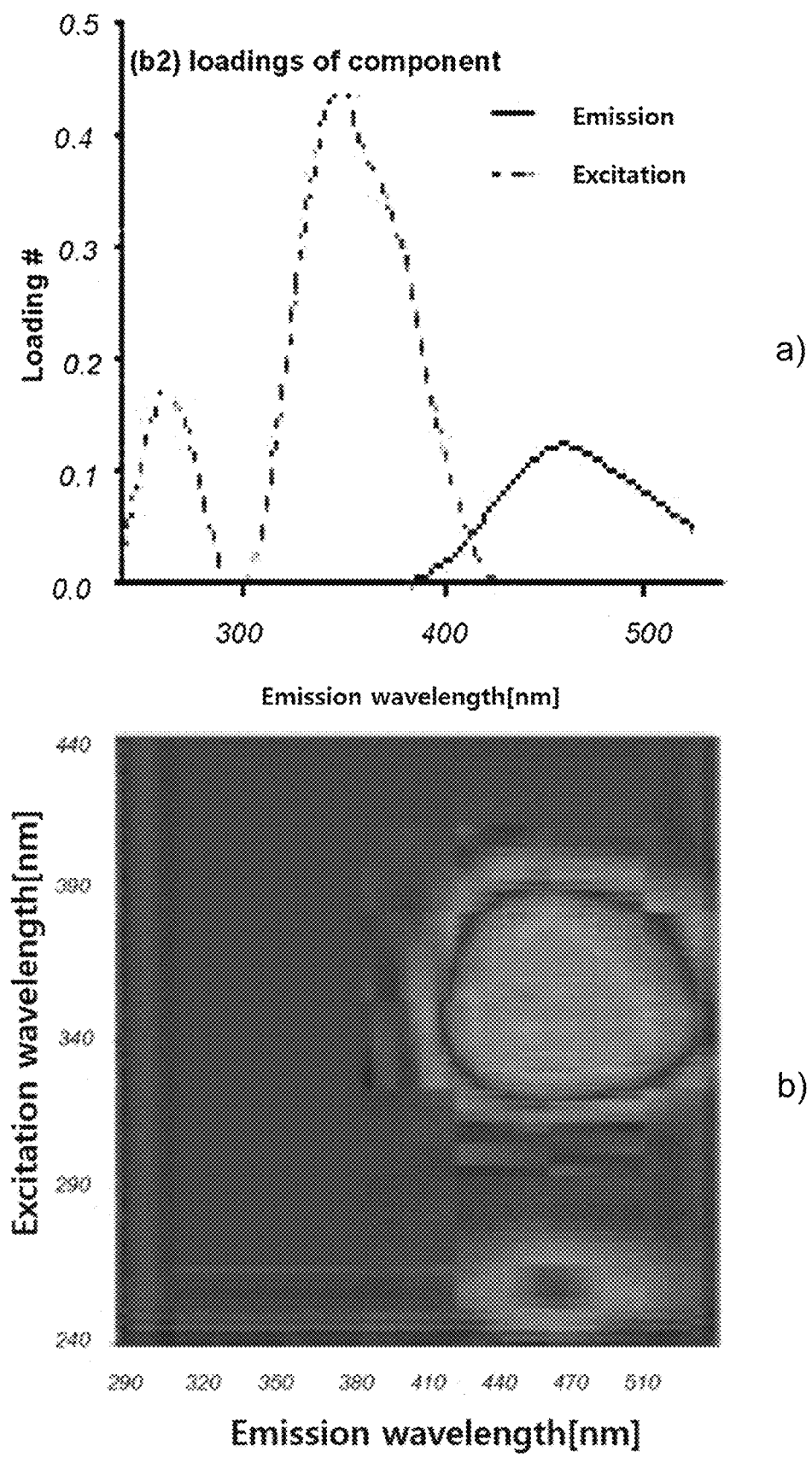
Figure 10:
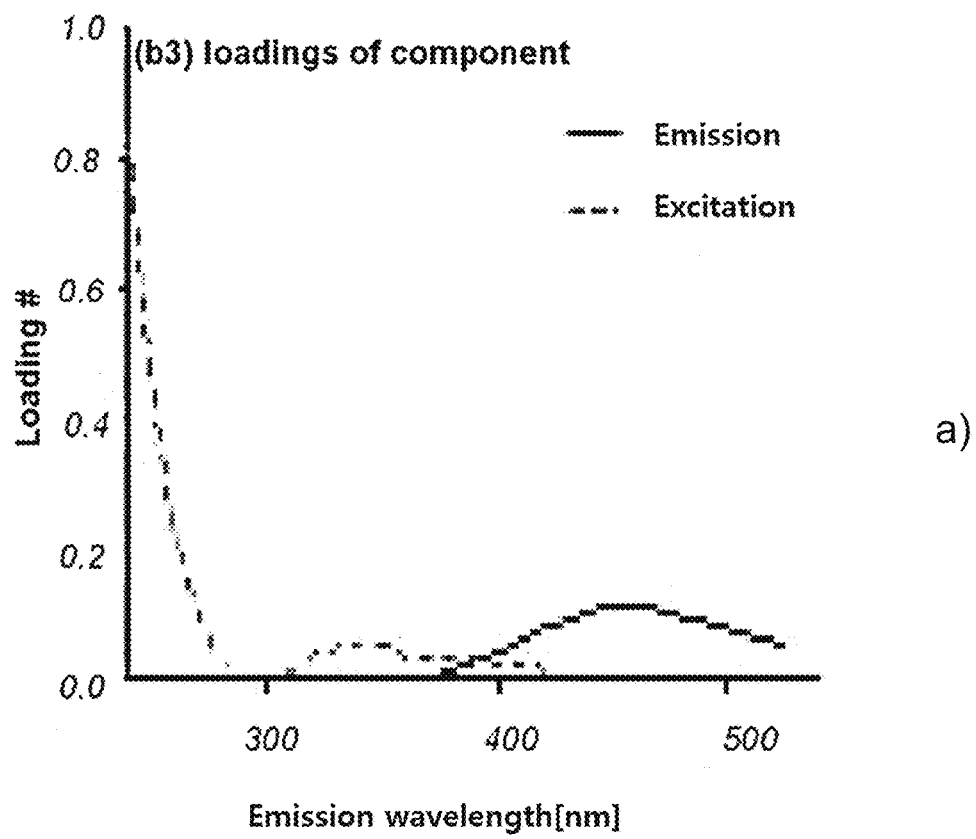
Figure 10:
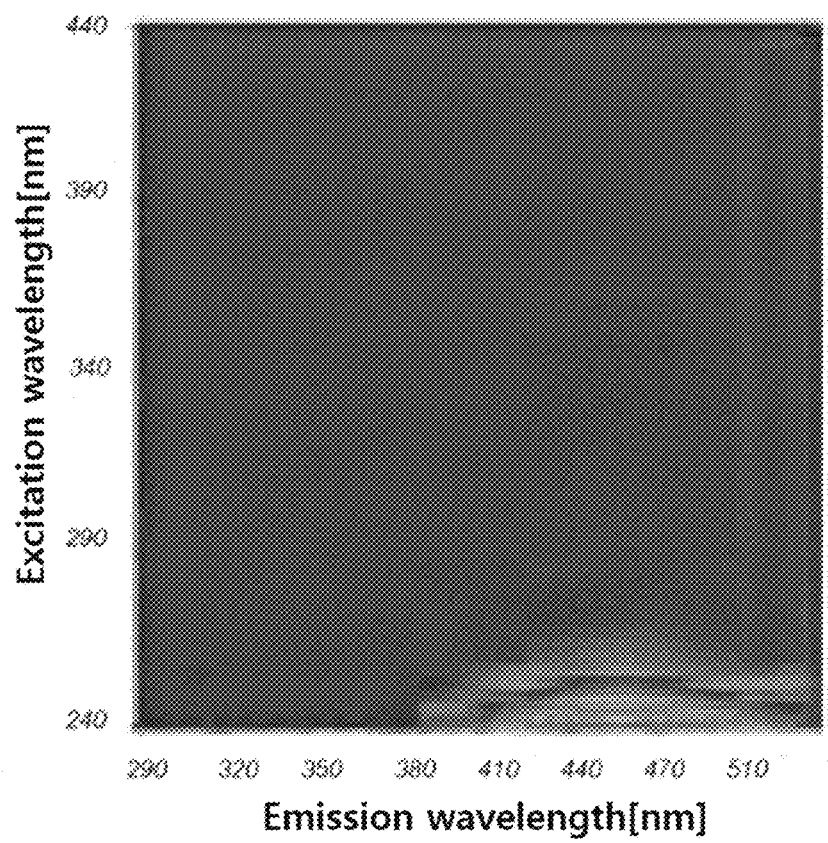
Figure 11:
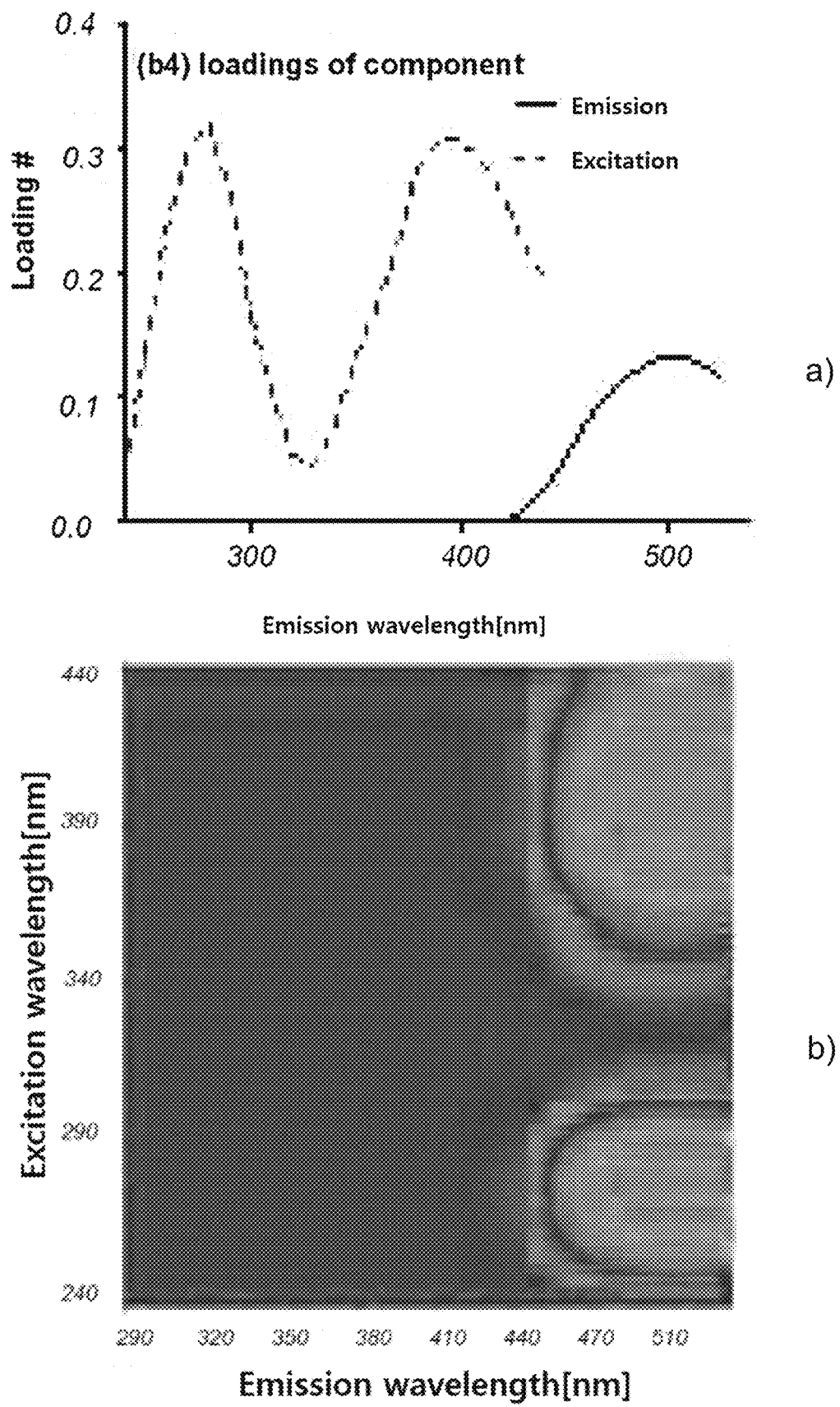
Figure 12:
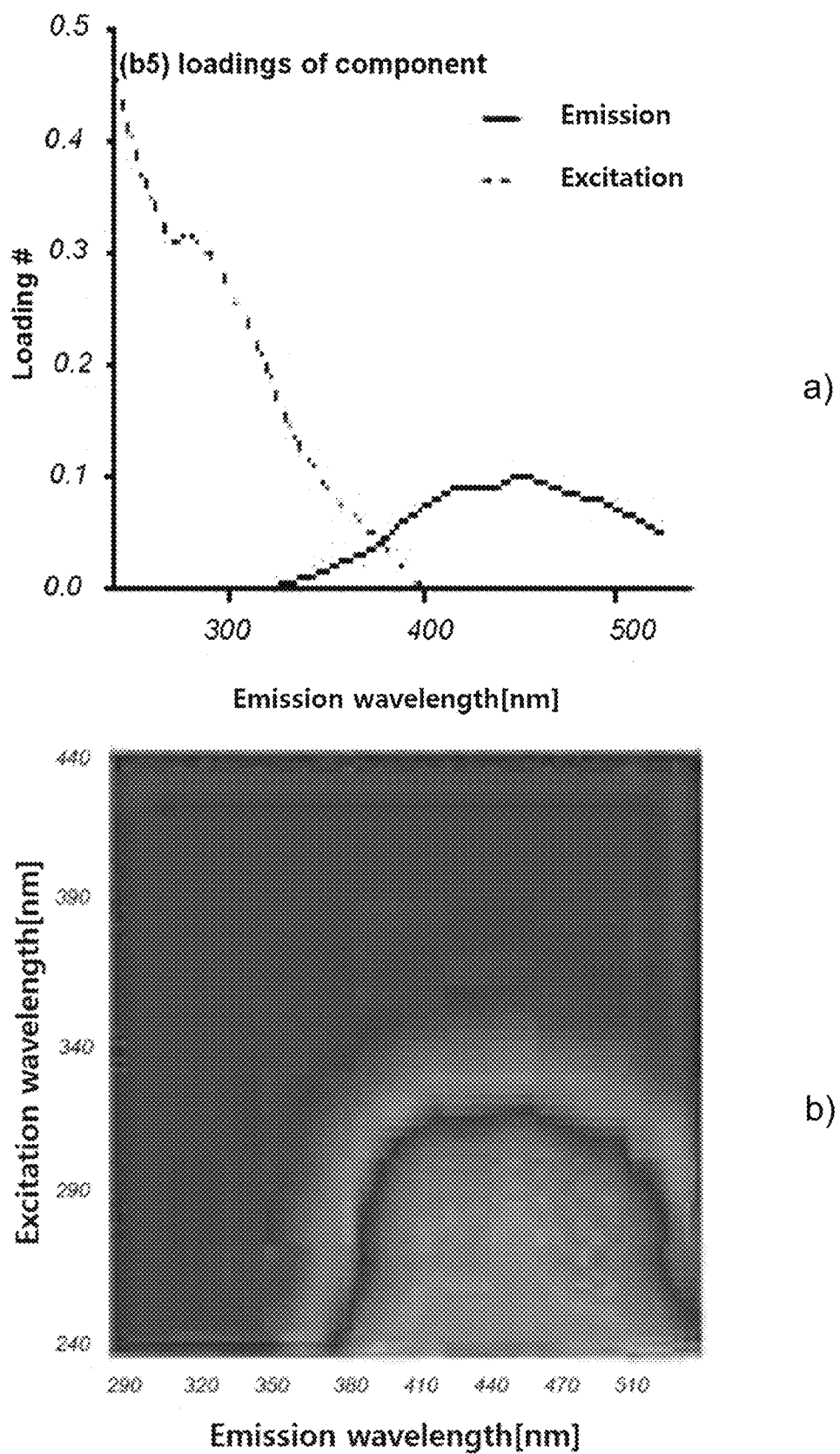

Meanwhile, FIG. 7 is a view for describing 3D-parallel factor (PARAFAC) modeling applied to a system for monitoring a hydroxyl radical scavenging index in water using a real-time multi-fluorescence analyzer and a parallel factor analysis apparatus according to exemplary embodiments of the present invention, and FIGS. 8 to 12 are views each illustrating the parallel factor (PARAFAC) modeling results of the parallel factor analysis apparatus in a system for monitoring a hydroxyl radical scavenging index in water using a real-time multi-fluorescence analyzer and a parallel factor analysis apparatus according to exemplary embodiments of the present invention.

Referring to FIG. 7, in the system for monitoring a hydroxyl radical scavenging index in water using a real-time multi-fluorescence analyzer and a parallel factor analysis apparatus according to exemplary embodiments of the present invention, the parallel factor analysis apparatus 130 classifies the EEM data by component for the multi-fluorescence analysis of the EEM data. Here, the parallel factor analysis apparatus 130 classifies the EEM data by first, second and third components by parallel factor (PARAFAC) modeling, wherein the first component classifies the EEM data using an excitation wavelength of 250 to 260 nm and an emission wavelength of 380 to 480 nm, the second component classifies the EEM data using an excitation wavelength of 330 to 350 nm and an emission wavelength of 420 to 480 nm, and the third component classifies the EEM data using an excitation wavelength of 270 to 280 nm and an emission wavelength of 320 to 350 nm.

As a method for analyzing a natural organic material (NOM), fluorescence excitation-emission matrices (F-EEMs) are used, and this is a method of measuring wavelength using the principle of fluorescence that emits light when the natural organic material (NOM) is stimulated, and distinguishing each natural organic material (NOM) component therefrom. The fluorescence components appearing in such a small number may be mathematically analyzed using parallel factor (PARAFAC) modeling.

Specifically, FIG. 7 is a simple graphic representation of a 3D-PARAFAC model, and referring to FIG. 7, the parallel factor modeling applies a 3D-PARAFAC model that three-dimensionally analyzes the EEM data by dividing the EEM data into each of three factors of a, b and c, wherein the EEM data array ($x_{ijk}$) of the 3D-PARAFAC model is given as $$x_{ijk} = \sum_{f=1}^{F} a_{if} b_{jf} c_{kf} + e_{ijk},$$

is represented by three matrices A, B and C having elements $a_{if}$, $b_{jj}$ and $c_{kj}$ in this case, and is established when the sum of error components ($e_{ijk}$.) becomes a minimum.

Accordingly, the system for monitoring a hydroxyl radical scavenging index in water using a real-time multi-fluorescence analyzer and a parallel factor analysis apparatus according to exemplary embodiments of the present invention may show each of the results of the parallel factor (PARAFAC) modeling, as illustrated in FIGS. 8 to 12.

After all, in the case of the system for monitoring a hydroxyl radical scavenging index in water using a real-time fluorescence analyzer and a parallel factor analysis apparatus according to exemplary embodiments of the present invention, the characteristics of an organic material in target water may be monitored through a continuous flow analysis method without using an existing indicator material rhodamine B. Accordingly, since it is possible to avoid the trouble of periodically washing the indicator material adsorbed into a reaction tube, a real-time multi-fluorescence analysis and measurement apparatus for automated monitoring of the hydroxyl radical requirement index in water may be provided.

In addition, according to exemplary embodiments of the present invention, in a water treatment system having an advanced oxidation process (AOP) applied thereto in which ozone, ultraviolet rays, hydrogen peroxide, and the like are combined, it is possible to simply calculate the hydroxyl radical scavenging index in the target water through an organic material characteristic index (fluorescence index) for each component obtained by classifying the characteristic structure of the organic material in water using real-time fluorescence analysis by means of a parallel factor (PARAFAC) model. Accordingly, the amount of chemical injection and the amount of ultraviolet irradiation, which are process control variables, may be controlled. Simultaneously, under given operating variable conditions, the removal rate of a target material in water is predicted, whereby the system may also be used as a diagnostic tool for process evaluation in the advanced oxidation process. Furthermore, according to exemplary embodiments of the present invention, the system may provide operational convenience that enables process control while reducing the amount of power consumed in the advanced oxidation process even though the type of target material and the water quality characteristics of raw water change.

[Method for Monitoring Hydroxyl Radical Scavenging Index in Water Using Real-Time Multi-Fluorescence Analyzer and Parallel Factor Analysis Apparatus]

Figure 13:
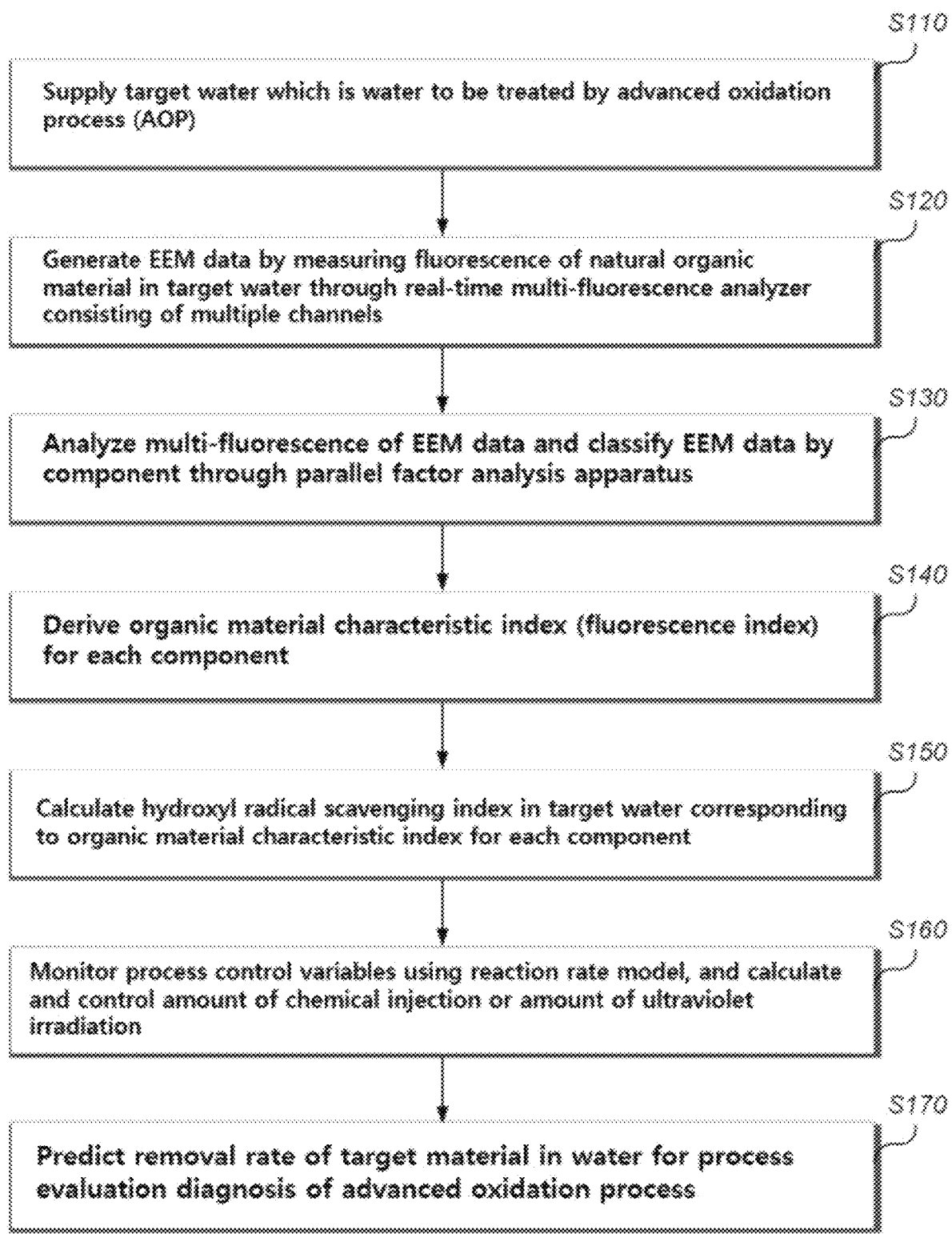
FIG. 13 is an operation flowchart of a method for monitoring a hydroxyl radical scavenging index in water using a real-time multi-fluorescence analyzer and a parallel factor analysis apparatus according to exemplary embodiments of the present invention.

FIG. 13 is an operation flowchart of a method for monitoring a hydroxyl radical scavenging index in water using a real-time multi-fluorescence analyzer and a parallel factor analysis apparatus according to exemplary embodiments of the present invention.

Referring to FIG. 13, in the method for monitoring a hydroxyl radical scavenging index in water using a real-time multi-fluorescence analyzer and a parallel factor analysis apparatus according to exemplary embodiments of the present invention, first, target water which is water to be treated by an advanced oxidation process (AOP) is supplied (S110). Here, the target water may be raw water to be treated by an advanced oxidation process (AOP) or treated water to be treated by an advanced oxidation process (AOP).

Next, excitation-emission matrix (EEM) data is generated by measuring the fluorescence of a natural organic material (NOM) in target water through a real-time fluorescence analyzer 120 consisting of multiple channels (S120). That is, the real-time multi-fluorescence analyzer 120 generates the EEM data using a plurality of fluorescence analyzers that emit three wavelength bands so as to measure the fluorescence of a natural organic material (NOM) in the target water.

Next, the EEM data is multi-fluorescence analyzed and classified by component through a parallel factor analysis apparatus 130 (S130). In this case, the parallel factor analysis apparatus 130 can classify the EEM data by first, second and third components by parallel factor (PARAFAC) modeling, wherein the first component may classify the EEM data using an excitation wavelength of 250 to 260 nm and an emission wavelength of 380 to 480 nm, the second component may classify the EEM data using an excitation wavelength of 330 to 350 nm and an emission wavelength of 420 to 480 nm, and the third component may classify the EEM data using an excitation wavelength of 270 to 280 nm and an emission wavelength of 320 to 350 nm.

Specifically, the parallel factor modeling applies a 3D-PRAFAC model that three-dimensionally analyzes the EEM data by dividing the EEM data into each of three factors of a, b and c, wherein the EEM data array ($x_{ijk}$) of the 3D-PARAFAC model is given as $$x_{ijk} = \sum_{f=1}^{F} a_{if} b_{jf} c_{kf} + e_{ijk}.,$$

is represented by three matrices A, B and C having elements $a_{if}$, $b_{jj}$ and $c_{kj}$ in this case, and is established when the sum of error components ($e_{ijk}$.) becomes a minimum.

Next, an organic material characteristic index (fluorescence index) for each component is derived (S140).

Next, a hydroxyl radical scavenging index in the target water corresponding to the organic material characteristic index for each component is calculated (S150).

Next, process control variables are monitored using a reaction rate model (S160). In this case, the amount of chemical injection or the amount of ultraviolet irradiation which is applied to the advanced oxidation process (AOP) may be calculated and controlled.

Next, the removal rate of a target material in water is predicted for the process evaluation diagnosis of the advanced oxidation process (S170).

According to the method for monitoring a hydroxyl radical scavenging index in water using a real-time multi-fluorescence analyzer and a parallel factor analysis apparatus according to exemplary embodiments of the present invention, the characteristics of the organic material in the target water can be monitored through a continuous flow analysis method, and in this case, a hydroxyl radical scavenging index in water is directly measured according to the organic material characteristic index for each component, which is derived through measurement and interpretation according to the fluorescence EEM (F-EEM) and parallel factor (PARAFAC) model of multiple wavelength bands consisting of multiple channels, and the hydroxyl radical scavenging index may be controlled by calculating the amount of chemical injection or the amount of ultraviolet irradiation, which is a process control variable.

After all, according to exemplary embodiments of the present invention, as a method for real-time measuring a hydroxyl radical scavenging index, the method may provide operational convenience that enables process control while reducing the amount of power consumed in the advanced oxidation process, and may also be quantitatively used in the chemical control of an advanced oxidation process which produces radicals.

The above-described description of the present invention is provided for illustrative purposes, and a person skilled in the art to which the present invention pertains will understand that the present invention can be easily modified into other specific forms without changing the technical spirit or essential features of the present invention. Therefore, it should be understood that the above-described embodiments are only illustrative in all aspects and not restrictive. For example, each constituent element which is described as a singular form may be implemented in a distributed form, and similarly, constituent elements which are described as being distributed may be implemented in a combined form.

The scope of the present invention is represented by the claims to be described below rather than the detailed description, and it should be interpreted that the meaning and scope of the claims and all the changes or modified forms derived from the equivalent concepts thereto fall within the scope of the present invention.

The invention claimed is:

1. A system for monitoring a hydroxyl radical scavenging index in water using a real-time multi-fluorescence analyzer and parallel factor analysis apparatus, the system comprising:
 a target water supply unit that supplies target water which is water to be treated by an advanced oxidation process (AOP);
 a real-time multi-fluorescence analyzer that consists of multiple channels and generates excitation-emission matrix (EEM) data by measuring the fluorescence of a natural organic material (NOM) in the target water;
 a parallel factor analysis apparatus that classifies the EEM data by a plurality of components by parallel factor (PARAFAC) modeling for the multi-fluorescence analysis of the EEM data;
 an organic material characteristic index derivation unit that derives an organic material characteristic index that is a fluorescence index for each of the plurality of components;
 a hydroxyl radical scavenging index calculation unit that calculates a hydroxyl radical scavenging index in the target water corresponding to the organic material characteristic index for each of the plurality of components; and
 a process control variable monitoring unit that monitors process control variables using a reaction rate model, wherein the process control variables comprise an amount of chemical injection or an amount of ultraviolet irradiation, which is applied to the advanced oxidation process (AOP), and
 wherein the characteristic index of the organic material in the target water is monitored through a continuous flow analysis method.

2. The system of claim 1, wherein the target water is raw water to be treated by the advanced oxidation process (AOP) or water to be treated by the advanced oxidation process (AOP).

3. The system of claim 1, wherein the real-time multi-fluorescence analyzer generates excitation-emission matrix (EEM) data using a plurality of fluorescence analyzers that emit three wavelength bands so as to measure the fluorescence of a natural organic material (NOM) in the target water.

4. The system of claim 3, wherein the parallel factor analysis apparatus classifies the EEM data by first, second and third components by the parallel factor (PARAFAC) modeling, the first component classifies the EEM data using an excitation wavelength of 250 to 260 nm and an emission wavelength of 380 to 480 nm, the second component classifies the EEM data using an excitation wavelength of 330 to 350 nm and an emission wavelength of 420 to 480 nm, and the third component classifies the EEM data using an excitation wavelength of 270 to 280 nm and an emission wavelength of 320 to 350 nm.

5. The system of claim 1, further comprising a target material removal rate prediction unit that predicts a removal rate of the target material in water for process evaluation diagnosis of the advanced oxidation process (AOP).

6. A method for monitoring a hydroxyl radical scavenging index in water using a real-time multi-fluorescence analyzer and a parallel factor analysis apparatus, the method comprising:
   a) supplying target water which is water to be treated by an advanced oxidation process (AOP);
   b) generating excitation-emission matrix (EEM) data by measuring a fluorescence of a natural organic material in the target water through a real-time multi-fluorescence analyzer consisting of multiple channels;
   c) analyzing multi-fluorescence of the EEM data and classifying the EEM data by a plurality of components by parallel factor (PARAFAC) modeling through a parallel factor analysis apparatus;
   d) deriving an organic material characteristic index that is a fluorescence index for each of the plurality of components;
   e) calculating a hydroxyl radical scavenging index in the target water corresponding to the organic material characteristic index for each of the plurality of components;
   f) monitoring process control variables using a reaction rate model, wherein the process control variables comprise an amount of chemical injection or an amount of ultraviolet irradiation, which is applied to the advanced oxidation process (AOP); and
   g) predicting a removal rate of a target material in water for process evaluation diagnosis of the advanced oxidation process, wherein the characteristic index of the organic material in the target water is monitored through a continuous flow analysis method.

7. The method of claim 6, wherein the target water in step a) is raw water to be treated by the advanced oxidation process (AOP) or treated water to be treated by the advanced oxidation process (AOP).

8. The method of claim 6, wherein the real-time multi-fluorescence analyzer in step b) generates excitation-emission matrix (EEM) data using a plurality of fluorescence analyzers that emit three wavelength bands so as to measure the fluorescence of a natural organic material (NOM) in the target water.

9. The method of claim 8, wherein the parallel factor analysis apparatus in step c) classifies the EEM data by first, second and third components by the parallel factor (PARAFAC) modeling, the first component classifies the EEM data using an excitation wavelength of 250 to 260 nm and an emission wavelength of 380 to 480 nm, the second component classifies the EEM data using an excitation wavelength of 330 to 350 nm and an emission wavelength of 420 to 480 nm, and the third component classifies the EEM data using an excitation wavelength of 270 to 280 nm and an emission wavelength of 320 to 350 nm.

* * * * *